(12) United States Patent
Cordill

(10) Patent No.: US 7,063,302 B2
(45) Date of Patent: Jun. 20, 2006

(54) SAMPLE VALVE WITH INTEGRAL SAMPLE SHUT OFF FUNCTION FOR CHROMATOGRAPH

(75) Inventor: Leroy D. Cordill, Bartlesville, OK (US)

(73) Assignee: Siemens Energy & Automation, Inc., Alpharetta, GA (US)

( * ) Notice: Subject to any disclaimer, the term of this patent is extended or adjusted under 35 U.S.C. 154(b) by 604 days.

(21) Appl. No.: 10/093,599

(22) Filed: Mar. 8, 2002

(65) Prior Publication Data

US 2002/0131905 A1    Sep. 19, 2002

Related U.S. Application Data

(60) Provisional application No. 60/275,532, filed on Mar. 13, 2001.

(51) Int. Cl.
F16K 31/12 (2006.01)
F16K 1/36 (2006.01)
F16K 3/32 (2006.01)
F16K 5/10 (2006.01)
B01L 11/00 (2006.01)

(52) U.S. Cl. .................. 251/208; 251/59; 251/205; 251/206; 251/207; 251/209; 251/286; 251/292; 73/1.01; 73/1.02; 73/1.72; 73/23.2; 137/247; 422/68.1; 422/70; 422/81; 422/82; 422/83; 422/100; 422/103; 436/43; 436/53; 436/180

(58) Field of Classification Search .............. 73/1.01, 73/1.02, 1.72, 23.2; 137/247; 422/68.1, 422/70, 81, 82, 83, 100, 103; 436/43, 53, 436/180; 251/59, 304, 205, 206, 207, 208, 251/209, 286, 292
See application file for complete search history.

(56) References Cited

U.S. PATENT DOCUMENTS

| | | | |
|---|---|---|---|
| 3,077,766 A | 2/1963 | Reinecke | 73/23 |
| 3,150,517 A | 9/1964 | Kuffer | 73/23.1 |
| 3,223,123 A | 12/1965 | Young | 137/625.46 |
| 3,744,219 A | 7/1973 | Stalling | 55/162 |
| 4,155,978 A * | 5/1979 | Naono et al. | 422/64 |
| 4,243,071 A | 1/1981 | Shackelford | 137/625.46 |
| 4,353,243 A | 10/1982 | Martin | 73/23.1 |
| 4,816,226 A * | 3/1989 | Jordan et al. | 422/81 |
| 5,405,585 A * | 4/1995 | Coassin | 422/100 |
| 5,601,115 A | 2/1997 | Broerman | 137/595 |
| 6,453,725 B1 * | 9/2002 | Dahlgren et al. | 73/23.42 |
| 6,701,774 B1 * | 3/2004 | Srinivasan et al. | 73/23.42 |

FOREIGN PATENT DOCUMENTS

| | | |
|---|---|---|
| EP | 0481285 A2 | 4/1992 |
| EP | 02 07 5994 | 7/2002 |
| WO | WO 98 11431 | 3/1998 |

* cited by examiner

*Primary Examiner*—Jill Warden
*Assistant Examiner*—Brian Sines

(57) ABSTRACT

A multiple port valve integrated with the function of the sample shut off valve is disclosed. The integration of the sample shut off function eliminates extra plumbing and labor costs associated with a separate sample shut off valve. Additionally, the multiple port valve integrated with the function of the sample shut off valve provides a shorter equilibration time and less tubing volume.

9 Claims, 3 Drawing Sheets

SAMPLE VALVE WITH INTEGRAL SAMPLE SHUT OFF FUNCTION FOR CHROMATOGRAPH

CROSS-REFERENCE TO RELATED APPLICATIONS

This application claims priority under 35 U.S.C. §119(e) to U.S. Provisional Application Ser. No. 60/275,532, entitled "Integrated Valve and Sample Shut-Off Valve System, Method and Apparatus," filed Mar. 13, 2001.

TECHNICAL FIELD

This invention relates generally to the field of chromatography, and more particularly for a multiple port valve with an integrated sample shut off function for a gas chromatograph.

BACKGROUND ART

A sample shut off valve is a common need in the gas chromatograph. The purpose of the sample shut off valve is to temporarily block the flow of the sample into the sample valve of the gas chromatograph. This allows the volume of vapor in the sample loop attached to the sample valve to equilibrate to atmospheric pressure prior to being injected into the chromatographic column when the sample valve is actuated. This reduces the influence of sample pressure on the quantified analytical results.

An implementation of the sample shut off valve function is to add a separate valve in the chromatograph oven. This valve is connected in series with the sample flow but is upstream of the sample valve. The sample shut off valve is then activated to block the flow for a period of a few seconds. The time is typically chosen to allow adequate time for the sample loop and all associated tubing paths downstream of the sample shutoff valve to equilibrate to atmospheric pressure.

The addition of the separate valve adds product costs due to the material cost of the valve, the labor for additional plumbing, and also consumes space in the gas chromatograph oven compartment.

Some valves available to the industry have an internal means of blocking the sample flow path prior to blocking the rest of the flow path prior to blocking the rest of the flow paths by having the parts situated such that the sample inlet port physically closes first when the valve mechanism is switched (typically a rotary or slider valve). Since the valve mechanism is directly coupled to the rest of the switching mechanism, the sample inlet flow is only blocked for a very short duration (<100 milliseconds). This does not allow adequate time to equilibrate the sample loop volume to atmospheric pressure.

Therefore, there is a significant need for a sample valve with an integrated sample shut off function.

SUMMARY OF THE INVENTION

According to one aspect of the invention, there is provided a multiple port valve apparatus for injecting a sample to be analyzed in to a column of a chromatograph that analyzes samples, said multiple port valve incorporating a sample shut off valve function, said multiple port valve apparatus comprising a plurality of ports, at least one of said ports receiving said sample to be analyzed by said chromatograph, a plurality of passages connecting said plurality of ports that transmit said sample between said plurality of ports, and a separately controlled passage that is independently controllable from said plurality of passages that responds to independent control and effects said sample shut off function by controlling an inlet of said sample to said sample loop of said chromatograph.

According to another aspect of the invention, there is provided a method for switching a multiple port valve that transmits a sample to be analyzed to a chromatograph that analyzes said sample valve having an independently switched sample flow passage incorporated therein for effecting a sample shut off function, said method comprising the steps of: inletting a sample to be analyzed into a first port of said multiple port valve, transmitting said sample inlet into said first port to said sample flow passage, and controlling said sample flow passage independently from other passages of said multiple port valve to control a flow of said sample through said sample flow passages to thereby effect said sample shut off valve function.

BRIEF DESCRIPTION OF THE FIGURES

The present invention will now be described with reference to the accompanying drawings wherein.

DETAILED DESCRIPTION OF THE FIGURES

The present invention relates to a multiple port valve integrated with the function of the sample shut off valve. While the present invention is applicable to any type of multiple port valve, the Siemens model 50 valve is recommended with the present invention. In comparison to the prior art, the shut off valve function is directly incorporated into the multiple port valve. The present invention reduces the cost of manufacture of such a gas chromatograph by eliminating the material cost of a separate sample shut off valve. Additionally, the labor cost of additional plumbing is eliminated. Additionally, additional oven space is not needed to accommodate the separate shut off valve. Additionally, the present invention provides a shorter equilibration time than with a separate shut off valve since, as will be described further, the present invention utilizes less tubing volume. As a result of this feature, there is less tubing required to equilibrate to atmospheric pressure prior to the sample inject operation of the sample valve.

In more detail, and as shown in the figures, the valve of the present invention is modified from an off-the-shelf valve, such as the Siemens model 50 sample valve. In one embodiment, the present invention is practiced by modifying the Model 50 sample valve by allowing one flow passage in the valve to be separately controlled from the remainder of the valve passages. With this arrangement, the single flow passage may be independently blocked. The valve is allowed to equilibrate and, after a predetermined time required for the pressure equilibration, the remainder of the valve passages, hereinafter referred to as normal valve passages, are switched. Thereby, sample inject operation into the column is effected.

Figure 1:
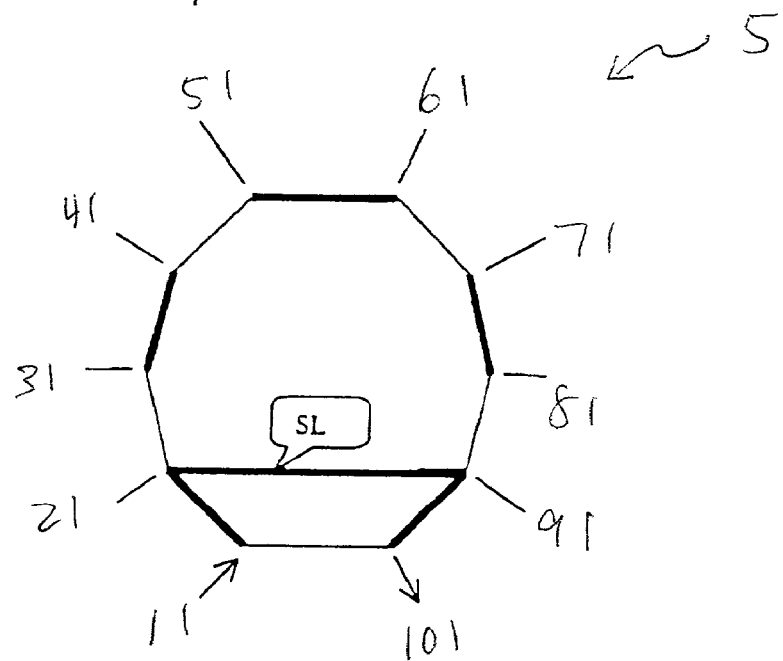
FIG. 1 is a schematic cross-section of a ten port valve in accordance with the present invention illustrating the path of the sample to be analyzed flowing through a sample loop.

The operation of an integrated sample shut off valve function is illustrated with reference to the figures. Generally, in operation, the multiple port valve incorporating a sample shut off valve function includes the following steps. In brief, a complete cycle typically includes three states of operation for the valves: stopping the sample flow, injecting the sample, and returning the valve to the original state where the sample may flow through the sample loop. Referring to FIG. 1, there is shown a schematic cross-section of an exemplary ten port valve 5 in accordance with the principles of the present invention. The ten ports are 11, 21, 31, 41, 51, 61, 71, 81, 91, 101 represent ports of the valve 5. In a first state, the shut off valve is considered to be in an off state, wherein the sample flows through sample loop (SL) as shown in the figure, while actuation pressure is applied to the bottom plate (not shown). In detail, with reference to FIG. 1, the sample is shown schematically flowing into port 11. Subsequently, the sample flows from port 11 to port 21. Through the sample loop, the sample flows from port 21 to port 91. From port 91, the sample flows to port 101. The sample then flows to vent (not shown). In sample flow terminology the operation can be considered to be in state one: valve "off", sample flowing through sample loop (actuation pressure applied to bottom plate). The sample flow path can be denoted as (1) sample in to port 11; (2) port 11 to port 21; (3) through the sample loop to port 91; (4) port 91 to port 101; (5) to vent.

Figure 2:
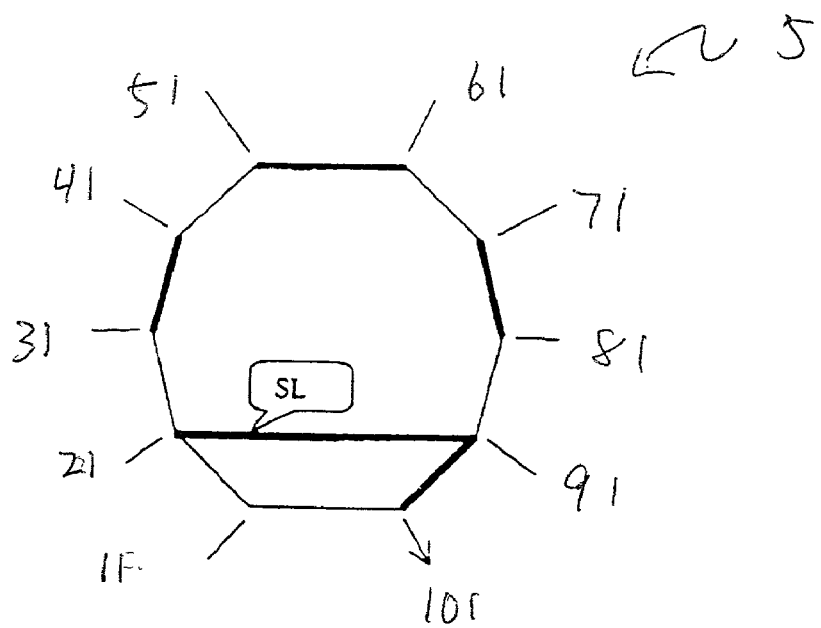
FIG. 2 is a schematic cross-section of a ten port valve in accordance with the principles of the present invention illustrating the path of the sample to be analyzed stopped and equilibrating in the sample loop.

In a second state of operation the valve is in an "off" state. The sample flow is blocked while actuation pressure is applied to the bottom plate (not shown) and to the sample shut off signal port on the top plate (not shown). Referring to FIG. 2, there is shown a schematic cross-section of an exemplary ten port valve 5 in accordance with the principles of the present invention. Identical reference numerals refer to the same elements of the figures. Here, the sample is injected into port 11. The flow between ports 11 and 21 is blocked in this state. The sample that had been in the sample loop continues to flow to port 91. The sample then flows from port 91 to port 101. The sample then flows to the vent (not shown). In sample flow terminology, the second state can be denoted as: sample into port 11; port 11 to port 21 is blocked; sample loop to port 91; port 91 to port 101; to vent.

Figure 3:
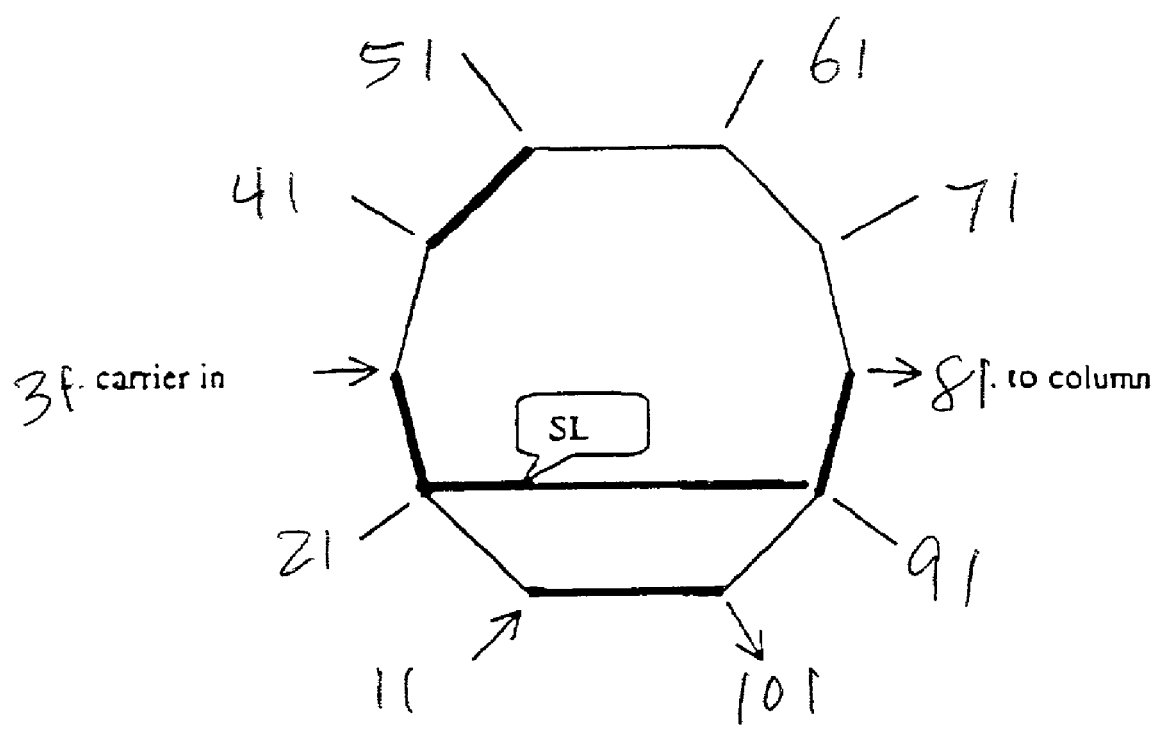
FIG. 3 is a schematic cross-section of a ten port valve in accordance with the principles of the present invention illustrating the path of the sample to be analyzed flowing through a sample loop.

In a third state, the valve is "on." The sample is injected into port 11 while the actuation pressure is applied to the top plate (not shown) and to sample shut off signal port on the top plate (not shown). Referring to FIG. 3, there is shown a schematic cross-section of an exemplary ten port valve 5 in accordance with the principles of the present invention. Identical reference numerals refer to the same elements of the figures. In the third state, the operation of the valve is illustrated herein. Here, the sample is injected into port 11. The sample flows from port 11 to port 101. Subsequently, the sample flows to the vent (not shown). The carrier is then injected into port 31. The carrier flows from port 31 to port 21. The carrier flows through the sample loop to port 91. The carrier flows from port 91 to 81. The carrier then flows to the column (not shown). In sample flow terminology, the third state can be denoted as: sample in to port 11; port 11 to port 101; to vent; carrier in to port 31; port 31 to port 21; sample loop to port 91; port 91 to port 81; to column.

The fourth state reverts to the second state. That is, the valve is in an "off" state. Referring back to FIG. 2, the sample flow is blocked while actuation pressure is applied to the bottom plate (not shown) and to the sample shut off signal port on the top plate (not shown). The sample flows into port 11. Flow between ports 11 and 21 is blocked. The sample flows through the sample loop to port 91. The sample then flows to port 91 to port 101. The sample then flows to the vent. In other terms, second state can be denoted as: sample into port 11; port 11 to port 21 blocked; sample loop to port 91; port 91 to port 101; to vent.

The fifth state reverts to the first state. In other words, the valve is in an "off" state wherein the sample flows through the sample loop as shown in the figures, while actuation pressure is applied to the bottom of the plate. Referring back to FIG. 1, in detail, the sample flows into port 11. Then, the sample flows from port 11 to port 21. Through the sample loop, the sample flows from port 21 to port 91. From port 91, the sample flows to port 101. The sample then flows to the vent (not shown). In sample flow terminology, the sample valve is in "off" state, sample flowing through the sample loop (with actuation pressure applied to the bottom plate), sample flow paths are illustrated as: sample in port 11: port 11 to port 21; through the sample loop to port 91; port 91 to port 101; to vent.

Figure 4:
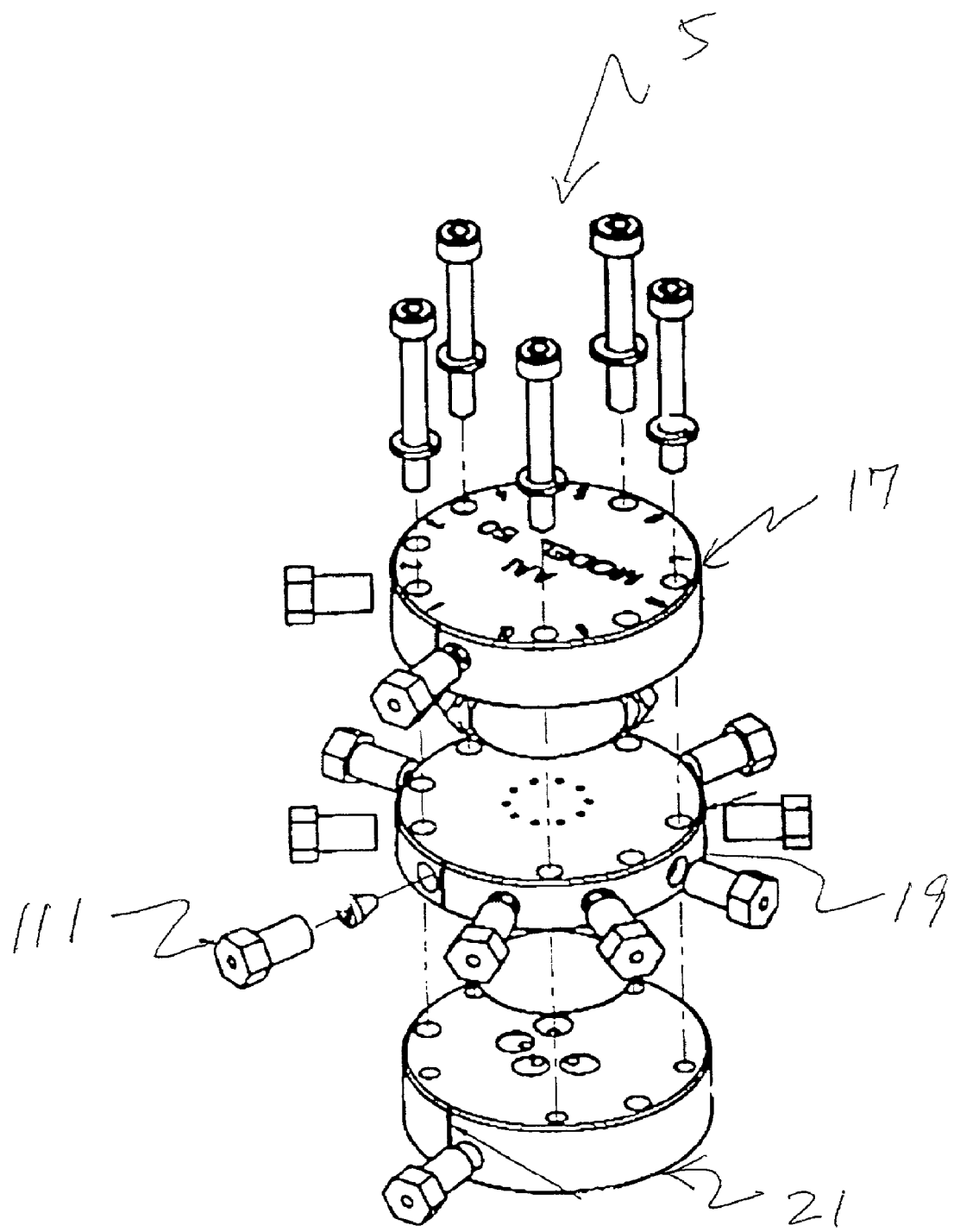
FIG. 4 is an isometric view of a ten port valve in accordance with the principles of the present invention.

Referring to FIG. 4, there is shown an isometric view of a ten port valve in accordance with the principles of the present invention. The multiport valve 5 of the present invention includes a top plate 17 and a bottom plate 21. Individual ports (exemplary port numbered 111 in the figure) are aligned in an outward arc around the middle plate 19.

It will be noted that the above relationship between the ports have been illustrated with respect to a ten port valve. The above relationship is suitable for a Siemens model 50 sample valve available from Siemens. Those of ordinary skill in the art may readily determine the suitable port relationships for a multiport apparatus of six ports or any suitable number of ports.

It will be appreciated that the above described embodiments are illustrative and that those of ordinary skill in the art may readily devise their own implementations that incorporate the principles of the present invention and fall within the spirit and scope thereof.

What is claimed is:

1. A multiple port valve apparatus for injecting a sample to be analyzed in to a column of a chromatograph that analyzes samples, said multiple port valve apparatus comprising:

a plurality of ports, at least one of said ports receiving said sample to be analyzed by said chromatograph;

a plurality of passages connecting said plurality of ports that transmit said sample between said plurality of ports; and a separately controlled passage that is independently controllable from said plurality of passages that responds to independent control;

wherein the separately controlled passage is configured to integrate a sample shut off valve function by controlling an inlet of the sample to said column of said chromatograph.

2. The apparatus of claim 1 wherein said multiple port valve apparatus is a ten port valve.

3. The apparatus of claim 1 wherein said multiple port valve apparatus is a six port valve.

4. The apparatus of claim 1, wherein said sample is a vapor and said separately controlled passage effects said sample shut off valve function by controlling an inlet of said vapor.

5. The apparatus of claim 1, wherein said separately controlled passage is selected such that a time period for equilibrating a pressure of said sample is optimized.

6. A method for switching a multiple port valve that transmits a sample to be analyzed to a chromatograph that analyzes said sample valve having an independently switched sample flow passage integrated therein for effecting a sample shut off valve function, said method comprising the steps of: inletting a sample to be analyzed into a first port of said multiple port valve; transmitting said sample inlet into said first port to said sample flow passage; and controlling said sample flow passage independently from other passages of said multiple port valve to control a flow of said sample through said sample flow passages to thereby effect said sample shut off valve function.

7. The method of claim 6, further comprising the step of selecting a volume of said sample valve such that a time period for equilibrating a pressure of said sample is optimized.

8. The method of claim 6, further comprising the steps of transmitting said sample inlet to said first port to a second port through said sample flow passage to a third port and transmitting said sample at said third port to a fourth port where the sample is vented.

9. The method of claim 8, further comprising the step of blocking the flow of said sample from said first port to said second port.

* * * * *